(12) United States Patent
Schoen et al.

(10) Patent No.: US 6,488,756 B1
(45) Date of Patent: *Dec. 3, 2002

(54) PIGMENT MIXTURE

(75) Inventors: Sabine Schoen, Darmstadt (DE); Reiner Vogt, Kranichstein (DE); Norbert Schül, Heppenheim (DE); Karl Osterried, Dieburg (DE); Uta Maurer, Darmstadt (DE)

(73) Assignee: Merck Patent Gesellschaft, Darmstadt (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/322,163

(22) Filed: May 28, 1999

(30) Foreign Application Priority Data

May 28, 1998 (DE) .......................................... 198 23 864

(51) Int. Cl.⁷ ............................................. C04B 14/00
(52) U.S. Cl. ........................ 106/415; 106/417; 106/410; 106/482
(58) Field of Search ................................ 106/415, 417, 106/410, 482

(56) References Cited

U.S. PATENT DOCUMENTS

| 5,441,564 A | | 8/1995 | Vogt | 106/417 |
| 5,667,580 A | * | 9/1997 | Babler | 106/415 |
| 5,735,939 A | * | 4/1998 | Glausch et al. | 106/415 |
| 5,749,946 A | * | 5/1998 | Glausch et al. | 106/417 |
| 5,843,220 A | * | 12/1998 | Babler | 106/415 |
| 6,190,445 B1 | * | 2/2001 | Noguchi | 106/31.9 |

FOREIGN PATENT DOCUMENTS

WO    WO93/08237    *    4/1993

* cited by examiner

Primary Examiner—Helene Klemanski
Assistant Examiner—Veronica F. Faison
(74) Attorney, Agent, or Firm—Millen, White, Zelano & Branigan, P.C.

(57) ABSTRACT

The present invention relates to pigment mixtures consisting of at least two components, component A being $SiO_2$ flakes coated with one or more metal oxides and/or metals and component B being platelet-shaped, acicular or spherical colorants or fillers, and to their use in particular in varnishes, paints, printing inks, powder coating materials, plastics and cosmetic formulations.

21 Claims, No Drawings

PIGMENT MIXTURE

Summary of the Invention

The present invention relates to pigment mixtures comprising at least two components, component A being $SiO_2$ flakes coated with one or more metal oxides and/or metals and component B being platelet-shaped, acicular or spherical colorants and/or fillers, and to their use in varnishes, paints, printing inks, plastics, powder coating materials and cosmetic formulations.

With platelet-shaped pigments, hiding power and gloss are often difficult to realize simultaneously to a satisfactory extent. For instance, $SiO_2$ flakes or mica platelets covered with one or more thin metal oxide layers feature interference colors and a high luster but at the same time, owing to the transparent substrate, feature high transparency and hence a comparatively poor hiding power.

DE-A-42 40 511 discloses a pigment mixture which is composed of an interference pigment and a platelet-shaped color pigment. The interference pigment comprises mica flakes or $SiO_2$ flakes coated with metal oxides and the color pigment can be colored $SiO_2$ flakes. This pigment mixture is incorporated into coating materials, printing inks or plastics.

It is an object of the present invention to provide a pigment mixture which is notable for a comparatively high hiding power, which lends itself well to incorporation into the respective system in which it is used and for which at the same time the separation of pigment/colorant in the system is minimal.

Surprisingly, a pigment mixture has now been found which has none of the disadvantages indicated above. The pigment mixture of the invention comprises at least two components, component A being $SiO_2$ flakes coated with one or more metal oxides and/or metals and component B being platelet-shaped, acicular or spherical colorants or fillers. By admixing the colorant to the coated $SiO_2$ flakes it is possible to give the systems in which they are used a multiple flop, the color effect is intensified, and new color effects are achieved. As used herein, the term "multiple flop" refer to color changes as a function of viewing angle.

The invention thus provides a pigment mixture comprising at least two components, component A being $SiO_2$ flakes coated with one or more metal oxides and/or metals and component B being platelet-shaped, acicular or spherical colorants or fillers. By spherical is meant a range of substantially spherical shapes including, e.g., perfect spheres, indented or deformed spheres, etc.

The invention likewise provides formulations, such as paints, varnishes, printing inks, plastics, powder coating materials and cosmetic formulations, which comprise the pigment mixture of the invention.

The coated $SiO_2$ flakes can be mixed with the colorant and/or filler in any ratio. Preferably, the (wt/wt) ratio of component A to component B is about 1:10 to 10:1, in particular about 1:2 to 2:1.

The $SiO_2$ flakes produced on a continuous belt in accordance with WO 93/08237 are based on a platelet-shaped, transparent, colored or colorless matrix and typically possess a thickness of about 0.1 to 5 µm, in particular about 0.2 to 2.0 µm. The length in the two other dimensions is typically about 1 to 250 µm, preferably about 2 to 100 µm and, in particular, about 5 to 40 µm. The $SiO_2$ flakes are provided with one or more metal oxide layers an/or metal layers. Examples of suitable metal oxides or metal oxide mixtures are, e.g., titanium oxide, zirconium oxide, zinc oxide, iron oxides and/or chromium oxide, especially $TiO_2$ and/or $Fe_2O_3$. The $SiO_2$ flakes can be coated as described, for example, in WO 93/08237 (wet chemical coating) or DE-A-196 14 637 (CVD process).

The outer metal oxide layer can also be a semitransparent metal layer. Metals suitable for this purpose are, for example, Cr, Ti, Mo, W, Al, Cu, Ag, Au and Ni. Metals can be coated on the $SiO_2$ flakes by conventional methods, e.g., physical vapor deposition (PVD). Preferred pigments have the following layer structure: $SiO_2$ flakes+metal+$SiO_2$+metal oxide.

In order to bring out special color effects, fine particles in the nanometer size range can be introduced into the metal oxide layers of high or low refractive index. Examples of pigments suitable for this purpose are, e.g., finely divided $TiO_2$ or finely divided carbon (carbon black) with particle sizes in the range of about 10 to 250 nm. Through the light-scattering properties of such particles it is possible to exert a controlled influence on luster and hiding power.

Colorants suitable as component B for the pigment mixture of the invention are all acicular and spherical colorants which are known to the skilled worker and have a particle size of about 0.001 to 10 µm, preferably about 0.01 to 1 µm. The pigment mixtures of the invention preferably comprise, as colorants, absorption materials and/or fillers.

The spherical colorants can be, e.g., $TiO_2$, colored $SiO_2$, $CaSO_4$, iron oxides, chromium oxides, carbon black or organic color pigments, such as anthraquinone, quinacridone, diketopyrrolopyrrole, phthalocyanine, azo and isoindoline pigments. The acicular pigments can be, e.g., BiOCl, colored glass fibers, -$Fe_3O_4$, or organic color pigments, such as azo pigments, β-phthalocyanine CI Blue 15.3, Cromophtal Yellow 8GN (Ciba-Geigy), Irgalith Blue PD56 (Ciba-Geigy), azomethine copper complex CI Yellow 129, and Irgazine Yellow 5GT (Ciba-Geigy).

Cosmetic formulations (especially decorative formulations) preferably comprise, not only colorants and $SiO_2$ flakes, but also fillers (one or more) or mixtures thereof in amounts (wt/wt) of about 1–50%, preferably about 1–30% and most preferably, about 1–15%, based on the overall solids content of the system.

Suitable fillers can be, e.g., mica, talc, $TiO_2$ and mica, $TiO_2$+$BaSO_4$+mica, mica+silica, silica, silica+$TiO_2$+$Fe_2SO_3$, BiOCl, BiOCl+mica, or BiOCl+talc. Some of these products are obtainable, e.g., under the trade names of Merck KGaA: Ronasphere®, Ronasphere® LDP, Micronasphere® M, Silk Mica, Satin Mica, Naturaleaf Powder, Low Luster Pigment, Extender W, Talkum feinst gepulvert [finely powdered talc], Biron®, Bital® and Mibiron®. Other fillers can be, e.g., nylon-12 (from Elf Atochem), nylon-6 (from Elf Atochem), boron nitride, Nylon Powder (from Elf Atochem), polyamide 12 (from Kobo), polyethylene (from Kobo), PTFE (from Presperse), lauroyl lysine (from Ikeda), polymethyl methacrylate (from Ikeda) or calcium aluminum borosilicate (from Presperse).

The pigment mixture of the invention is simple and easy to handle. The pigment mixture can be incorporated into the system in which it is used simply by stirring it in. Laborious milling and dispersing of the pigments is not necessary.

The pigment mixture of the invention can be used, e.g., for pigmenting coating materials, printing inks, plastics, agricultural films, the coating of seeds, food colorings, button pastes, medicament coatings or cosmetic formulations. The concentration of the pigment mixture in the system in which it is to be used for pigmenting is typically about 0.1 to 70% by weight, preferably about 0.1 to 50% by weight and, in particular, about 1.0 to 10% by weight, based on the overall solids content of the system. It is generally dependent on the specific application.

Plastics comprising the pigment mixture of the invention in amounts of about 0.01 to 50% by weight, in particular about 0.1 to 7% by weight, based on the overall solids content of the system, are notable for a particular sparkle effect.

In the coating sector, especially in automotive finishing, the pigment mixture can be employed—for 3-coat systems as well—in amounts of about 0.1 to 10% by weight, preferably about 1 to 3% by weight, based on the overall solids content of the system. The proportion in which the coated $SiO_2$ flakes are mixed with component B depends on the desired effect. The $SiO_2$ flakes are preferably employed with component B in a proportion (wt/wt) of about 1:4, in particular of about 1:3.

In a coating material, the pigment mixture of the invention has the advantage that the desired color flop effect is achieved by a single-layer coating (one-coat system or base coat in a two-coat system). This color flop is extremely pronounced even under diffuse light. In comparison with coating systems which comprise a mica-based interference pigment rather than the coated $SiO_2$ flakes, coating systems with the pigment mixture of the invention exhibit a more marked depth effect and a glitter effect.

The pigment mixture of the invention can also be employed in decorative and grooming cosmetology. For this embodiment, component B colorants can be, e.g., organic or inorganic color pigments or dyes, of natural or synthetic origin, such as, e.g., chromium oxide, ultramarine, or spherical $SiO_2$ or $TiO_2$ pigments. The concentration of the components and the proportion of $SiO_2$ flakes to component B are dependent on the medium in which they are used and on the effect that is to be achieved. The $SiO_2$ flakes can be mixed with component B pigments in any proportions, the preferred ratio being about 1:10 to 10:1 (wt/wt). The use concentration of $SiO_2$ flakes can range from about 0.01% by weight in a shampoo to about 70% by weight in a compact powder, based on the overall solids content of the system. In the case of a mixture of $SiO_2$ flakes with spherical fillers, such as $SiO_2$, the concentration in the formulation can be about 0.01 to 70% by weight. The cosmetic products, such as nail varnishes, lipsticks, compact powders, shampoos, loose powders and gels, are notable for particularly interesting luster effects and/or color effects. The glitter effect in nail varnish can be increased markedly relative to conventional nail varnishes with the aid of the pigment mixtures of the invention. Furthermore, the pigment mixture of the invention can be employed in bath products, in toothpastes and for enhancing foods, for example as a mass colorant or as a coating.

In the pigmentation of binder systems for, for example, paints and printing inks for intaglio, offset or screen printing, or as a precursor for printing inks, in the form for example of highly pigmented pastes, granules, pellets, etc., pigment mixtures, especially those comprising coated $SiO_2$ flakes with spherical colorants, such as $TiO_2$, carbon black, chromium oxide, iron oxide or organic color pigments, have been found particularly suitable. The pigment mixture is typically incorporated into the printing ink in amounts of about 2 to 35% by weight, preferably about 5 to 25% by weight and, in particular, about 8 to 20% by weight, based on the overall solids content of the system. Offset printing inks may comprise the pigment mixture in an amount of up to about 40% by weight or more. The precursors of printing inks, in the form for example of granules, pellets, briquettes, etc., can contain up to about 95% by weight of the pigment mixture of the invention, not including the binder and additives. The mixing ratio of component A to component B is preferably about 1:10 to 10:1. The printing inks comprising the pigment mixture of the invention exhibit purer hues and their printability is improved owing to the good viscosity values.

The invention hence also provides formulations comprising the pigment mixture of the invention.

In the foregoing and in the following examples, all temperatures are set forth uncorrected in degrees Celsius; and, unless otherwise indicated, all parts and percentages are by weight.

The entire disclosure of all applications, patents and publications, cited above and below, and of German application No. 198 23 864.9 filed May 28, 1998 is hereby incorporated by reference.

The examples which follow are intended to illustrate the invention without, however, limiting it.

EXAMPLES

Example 1

Printing Ink

The pigment is incorporated into the solvent-containing binder by stirring at 600 rpm and the printing inks are subsequently knife-coated onto black-and-white cards.

Ink No. 1
88.0 g of Gebr. Schmidt 95 MB 011 TW
10.0 g of $Fe_2O_3$-coated $SiO_2$ flakes of particle size 5 to 40 µm
2.0 g of Gebr. Schmidt 95 MB 022-TW (Green)

Ink No. 2: Comparison
88.0 g of Gebr. Schmidt 95 MB 011 TW
10.0 g of $Fe_2O_3$-coated mica of particle size 10 to 60 µm
2.0 g of Gebr. Schmidt 95 MB 022-TW (Green)

The color card with Ink No. 1 exhibits in visual terms a markedly better color flop than the color cards with the comparison Ink No. 2.

Example 2

Automotive Finish

| | |
|---|---|
| 2.0 g | of $Fe_2O_3$-coated $SiO_2$ flakes of particle size 5–40 µm |
| 1.5 g | of Heliogen Blue L 6930 |
| 0.2 g | of Hostaperm Green 8G |
| 0.05 g | of pigment-grade carbon black FW 200 |
| 66.6 g | of basecoat (A4) MP system (FK = 19%) |
| 29.65 g | of diluent mixture |

A hue is achieved with a very pronounced blue-to-green flop and gold highlights which has the ability to change even towards dark violet.

Example 3

Plastic

Granules of the plastics polypropylene PP Stamylan PPH10 (from DSM) and polystyrene 143E (from BASF) are admixed in each case with a) 1% of $Fe_2O_3$-coated $SiO_2$ flakes of particle size 5 to 40 µm
b) a mixture of 1% of $Fe_2O_3$-coated $SiO_2$ flakes of particle size 5 to 40 µm and 0.1% of PV Fast Blue B2G01 (Pigment Blue 15.3 from Clariant)

c) 1% of $Fe_2O_3$-coated mica of particle size 10 to 60 μm d) a mixture of 1% of $Fe_2O_3$-coated mica of particle size 10 to 60 μm and 0.1% of PV Fast Blue B2G01 (Pigment Blue 15.3 from Clariant)

The pigmented granules are subsequently processed on an injection molding machine to form small stepped plates. The differences between the two plastics are slight, so that only one qualitative statement valid for both materials is made in the table below:

|  | Experiment 3a | Experiment 3b | Experiment 3c | Experiment 3d |
|---|---|---|---|---|
| Color at the specular angle near to 0° | reddish | reddish-grey | yellowish | greenish |
| Color at the specular angle near to 80° | yellowish brownish | yellow-green | reddish | blue-green |

The combination of a blue pigment with in each case one luster pigment ($SiO_2$ or mica-based) emphasizes very well how different the flop of the two luster pigments is.

Example 4

Eyeshadow

| Phase A | |
|---|---|
| 5.00% | Ronasphere ® (silica from Merck KGaA) |
| 25.00% | $TiO_2$-coated $SiO_2$ flakes of particle size 5 to 40 μm (from Merck KGaA) |
| 5.00% | CI Pigment Green 18 (CI77289) |
| 47.42% | Talc |
| 7.18% | Solanum Tuberosum (potato starch) |
| 2.40% | Magnesiu stearate |
| Phase B | |
| 6.96% | Isopropyl stearate |
| 0.40% | Cetyl palmitate |
| 0.40% | Petrolatum |
| 0.08% | Preservative |

The constituents of phase A are combined and formed into a premix. The melted phase B is then added dropwise with stirring to the powder mixture. The powders are pressed at 40–50 bar.

Example 5

Lipstick

| Phase A | |
|---|---|
| 8.25% | Cera alba |
| 4.95% | Ceresin, Copernica Cerifera |
| 3.30% | Lanolin oil |
| 5.28% | Isopropyl myristate |
| 1.98% | Mineral Oil |
| 0.03% | Tocopherol, ascorbyl palmitate, ascorbic acid, citric acid, PEG-8 |
| 0.06% | Preservative |
| 0.50% | Aroma |
| 1.00% | Lithol rubine BK, C.I. Pigment Red 57:1 (CI 15850) |
| ad 100.00% | Ricinus Communis (20% in castor oil) |
| Phase B | |
| 2.00% | Ronasphere ® (silica from Merck KGaA) |

| | -continued |
|---|---|
| 15.00% | Iron oxide-coated $SiO_2$ flakes of particle size 5 to 40 μm (from Merck KGaA) |

The constituents of phase A are heated to 75° C. and melted. The pigments of phase B are added and the entire batch is stirred thoroughly. The lipstick composition is then stirred for 15 minutes in the casting apparatus, which has been preheated to 65° C. The homogeneous melt is poured into the casting molds, which have been preheated to 65° C. The molds are then cooled and the cold moldings removed.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

We claim:

1. A pigment mixture comprising a component A, which comprises undoped and transparent flakes consisting essentially of $SiO_2$, which are coated with one or more metal oxides and/or metals, and a component B, which comprises a platelet-shaped, acicular or spherical colorant, or a filler.

2. The pigment mixture according to claim 1, wherein said metal oxide is titanium oxide, zirconium oxide, zinc oxide, iron oxide and/or chromium oxide.

3. The pigment mixture according to claim 1, wherein said metal is Cr, Ti, Mo, W, Al, Cu, Ag, Au and/or Ni.

4. The pigment mixture according to claim 1, wherein said $SiO_2$ flakes are coated with $TiO_2$ and/or $Fe_2O_3$.

5. The pigment mixture according to claim 1, wherein component B comprises $TiO_2$, colored $SiO_2$, $CaSO_4$, iron oxide, chromium oxide, colored glass particles, carbon black, silica, anthraquinone, quinacridone, diketopyrrolopyrrole, phthalocyanine, an azo pigment, an isoindoline pigment, BiOCl, colored glass fibers, $Fe_3O_4$, β-phthalocyanine, and/or an azomethine copper complex.

6. The pigment mixture according to claim 1, wherein the ratio of component A to component B is 10:1 to 1:10 by weight.

7. The pigment mixture according to claim 6, wherein said ratio of component A to component B is 1:2 to 2:1.

8. The pigment mixture according to claim 1, wherein said $SiO_2$ flakes are 0.2 to 2.0 μm thick.

9. The pigment mixture according to claim 1, wherein the length of said $SiO_2$ flakes is 5 to 40 μm.

10. The pigment mixture according to claim 1, wherein said colorant and/or filler is acicular or spherical particles which are 0.01 to 1 μm in size.

11. The pigment according to claim 1, further comprising, in said metal oxide coating, particles of finely divided $TiO_2$ or finely divided carbon, wherein said particles are 10 to 250 nm in diameter.

12. A varnish, paint, printing ink, plastic, powder coating material for coloring seed, cosmetic formulation or a food comprising the pigment mixture according to claim 1.

13. An automotive finish comprising the pigment mixture according to claim 1.

14. The cosmetic formulation of claim 12, further comprising a filler, which is 1 to 15% by weight of said cosmetic formulation, based on the overall solids content of the system.

15. The cosmetic formulation of claim 14, wherein said filler is mica, talc, $TiO_2$+mica, $TiO_2$+$BaSO_4$+mica mica+silica, silica, silica+$TiO_2$+$Fe_2O_3$, BiOCl, BiCl+mica, or BiOCl +talc.

16. The varnish, paint, printing ink, plastic, powder coating material for coloring seed, cosmetic formulation or food according to claim 12, wherein said pigment mixture is 1.0 to 10% by weight, based on the overall solids content of the system.

17. The plastic according to claim 12, wherein said pigment mixture is 0.1 to 7% by weight, based on the overall solids content of the system.

18. The automotive finish according to claim 13, wherein said pigment mixture is 1 to 3% by weight, based on the overall solids content of the system.

19. The automotive finish according to claim 13, wherein the ratio of component A to component B is 1:3.

20. The printing ink according to claim 12, wherein said pigment mixture is 8 to 20% by weight, based on the overall solids content of the system.

21. A formulation comprising a pigment mixture according to claim 1.

* * * * *